United States Patent [19]

Sauer et al.

[11] Patent Number: 4,766,128

[45] Date of Patent: Aug. 23, 1988

[54] OPTIONALLY 11- TO 13-SUBSTITUTED ERGOLINE COMPOUNDS USEFUL AS MEDICINAL AGENTS

[75] Inventors: Gerhard Sauer; Gregor Haffer; Helmut Wachtel; Herbert H. Schneider; Wolfgang Kehr, all of Berlin, Fed. Rep. of Germany

[73] Assignee: Schering Aktiengesellschaft, Berlin and Bergkamen, Fed. Rep. of Germany

[21] Appl. No.: 589,376

[22] Filed: Mar. 14, 1984

[30] Foreign Application Priority Data

Mar. 14, 1983 [DE] Fed. Rep. of Germany ....... 3309493

[51] Int. Cl.[4] ..................... A61K 31/48; C07D 457/12
[52] U.S. Cl. ........................................ 514/288; 546/68
[58] Field of Search ...................... 548/68; 260/239 E

[56] References Cited

U.S. PATENT DOCUMENTS

| | | |
|---|---|---|
| 3,646,046 | 2/1972 | Arcamone et al. ................. 424/261 |
| 3,821,226 | 6/1974 | Fehr et al. ........................... 424/261 |
| 3,992,385 | 11/1976 | Bach et al. .......................... 424/261 |

FOREIGN PATENT DOCUMENTS

| | | |
|---|---|---|
| 48695 | 3/1982 | European Pat. Off. . |
| 3308719 | 9/1983 | Fed. Rep. of Germany . |
| 959261 | 5/1964 | United Kingdom ................. 546/67 |
| 2093452 | 9/1982 | United Kingdom ................ 424/261 |
| 4116548 | 9/1983 | United Kingdom ................ 424/261 |

OTHER PUBLICATIONS

Guyton, Arthur C., *Textbook of Medical Physiology*, W. B. Saunders, Philadelphia (1981) p. 707.

Berde and Schild, *Ergot Alkaloids and Related Compounds*, Springer–Verlang, New York (1978), pp. 53–54.

*Primary Examiner*—Donald G. Daus
*Assistant Examiner*—Cecilia Shen
*Attorney, Agent, or Firm*—Millen & White

[57] ABSTRACT

Substituted ergolines of the formula and their acid addition salts, wherein
the urea side chain in the 8-position can be in the $d\alpha$- or $\beta$-configuration, $C_2 = C_3$ and $C_9 = C_{10}$ are a CC single or C=C double bond, and
R is hydrogen or NR'R" wherein R'R" is $O_2$, $H_2$, $C_{1-4}$-dialkyl, or, together, they form a 3- to 9-membered ring, or R' and R" individually are hydrogen, $C_{1-4}$-alkyl, or $C_{1-10}$-acyl,
$R^1$ is hydrogen, $C_{1-4}$-alkyl, $C_{1-10}$-acyl, $C_{6-8}$-aryl, or $C_{1-4}$-alkylsulfonyl,
$R^2$ is hydrogen or halogen if $C_2 = C_3$ is a C=C double bond, or hydrogen if $C_2 = C_3$ is a CC single bond,
$R^6$ is $C_{1-4}$-alkyl,
show a pronounced effect on the central nervous system and are suitable, for example, as antidepressants, neuroleptics, or antihypertensives.

24 Claims, No Drawings

OPTIONALLY 11- TO 13-SUBSTITUTED ERGOLINE COMPOUNDS USEFUL AS MEDICINAL AGENTS

BACKGROUND OF THE INVENTION

The present invention relates to novel ergoline derivatives, a process for their preparation, and medicinal agents based on them.

Ergolines with substituents in the aromatic portion of the molecule, i.e., in positions 12 and 14, are known, for example, from U.S. Pat. No. 3,992,385 and GB No. 2,093,452.

SUMMARY OF THE INVENTION

It is an object of this invention to provide new such compounds having valuable pharmacological properties.

Upon further study of the specification and appended claims, further objects and advantages of this invention will become apparent to those skilled in the art.

These objects have been attained by providing new substituted ergolines of Formula I <chemical structure with NHCONEt$_2$, positions 8, 9, 10, 3, 2, N-R$^6$, R substituent, R$^1$-N, R$^2$> (I)

and their physiologically acceptable acid addition salts, wherein the urea side chain in the 8-position can be in the α- or β-configuration, $C_2\text{---}C_3$ and $C_9\text{---}C_{10}$ can be a CC single or C=C double bond, R is hydrogen or NR'R", wherein R'R" are $O_2$, $H_2$, $C_{1-4}$-dialkyl, or, together, form a 3- to 9-membered ring, or R' and R" individually independently are hydrogen, $C_{1-4}$-alkyl, or $C_{1-10}$-acyl, $R^1$ is hydrogen, $C_{1-4}$-alkyl, $C_{1-10}$-acyl, $C_{6-8}$-aryl or $C_{1-4}$-alkylsulfonyl, $R^2$ is hydrogen or halogen when $C_2\text{---}C_3$ is a C=C double bond, or hydrogen when $C_2\text{---}C_3$ is a CC single bond, and $R^6$ is $C_{1-4}$-alkyl.

DETAILED DISCUSSION

The acid addition salts of the compounds of this invention are derived from physiologically unobjectionable acids. Such physiologically unobjectionable acids include inorganic acids, such as, for example, hydrochloric acid, nitric acid, phosphoric acid, sulfuric acid, hydrobromic acid, hydriodic acid, nitrous acid, or phosphorus acid, or organic acids, such as, for example, aliphatic mono- or dicarboxylic acids, phenyl-substituted alkanecarboxylic acid, hydroxyalkanecarboxylic acids, or alkanedicarboxylic acids, aromatic acids, or aliphatic or aromatic sulfonic acids. Physiologically acceptable salts of these acids include, therefore, e.g., the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluorine, acetate, propionate, decanoate, caprylate, acrylate, formate, isobutyrate, caproate, heptanoate, propiolate, malonate, succinate, suberate, sebacate, furmarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, and naphthalene-2-sulfonate.

All the alkyl residues of up to 4 carbon atoms are those derived from the aliphatic hydrocarbons, for example, methyl, ethyl, n-propyl, isopropyl, n-butyl, isobutyl, and tert.-butyl. "Alkyl" herein is intended to include $C_{3-4}$-cycloalkyl groups as well as cyclopropylmethyl and methylcyclopropyl.

If R'R" on the amino nitrogen forms a 3- to 9-membered ring it is via a $C_{2-10}$-alkyl group, e.g., the substituent R is, for example, an aziridine, pyrrolidine, or piperidine ring, e.g., all members are C-atoms except for the connecting N-atom and the ring can also be substituted by alkyl groups, the total number being 2–10.

Suitable acyl groups include acid residues, e.g., alkanoyl of up to 5 carbon atoms or aroyl and aralkanoyl of 7–10 carbon atoms. Suitable alkanoyl residues of 1–5 carbon atoms are derived from aliphatic carboxylic acids which are physiologically compatible, for example, acetyl, propanoyl, n-butanoyl, isobutanoyl, etc. Suitable aroyl residues and aralkanoyl residues of 7–10 carbon atoms include, for example, benzoyl, p-methylbenzoyl, 3,5-dimethylbenzoyl, phenylacetyl, phenylpropanoyl, and p-tolylacetyl.

Examples of suitable $C_{1-4}$-alkyl- and $C_{6-8}$-arylsulfonyl residues include methanesulfonyl and p-toluenesulfonyl.

Suitable halogen atoms preferably are chlorine and bromine.

The 9,10-didehydroergolinylurea derivatives of this invention exhibit, as compared with 3-(9,10-didehydro-6-methyl-8α-ergolinyl)-1,1-diethylurea, a lesser pronounced or even a missing central dopaminergic activity (parameter: stereotypies), more pronounced adrenergic stimulation symptoms (parameter: piloerection), and in association therewith weaker or missing adrenolytic effects (parameter: erythema). Consequently, these compounds are suitable for use, for example, as geriatric agents and antidepressants, and also as antihypertensives, in therapeutic applications.

The ergolinylurea derivatives of this invention show, as compared with 3-(6-methyl-8α-ergolinyl)-1,1-diethylurea, a lesser pronounced adrenolytic activity (parameter: erythema), a more pronounced cataleptogenic effect and a more pronounced hypothermal effect. Thus, these compounds can be used, for example, as neuroleptics with less pronounced extrapyramidal and neuroendocrine side effects and for the treatment of extrapyramidal-motoric motion anomalies (dystonias, tardive dyskinesias, Huntington's disease).

The pharmacological efficacy of the ergolinylurea and 9,10-didehydroergolinylurea derivatives of this invention was tested conventionally in selected parameters of the mouse screen (mod. acc. to Irwin, S., Psychopharmacologia 13: 227–227, 1968). The lowest, fully effective dose (effect in at least two out of three animals) was determined in one of the aforementioned parameters after a one-time i.p. administration.

In order to utilize the compounds of this invention as medicinal agents, they are placed into the shape of a pharmaceutical preparation containing, in addition to the active agent, pharmaceutical, organic or inorganic, inert excipients suitable for enteral or parenteral administration, such as, for example, water, gelatin, gum arabic, lactose, amylose, magnesium stearate, talc, vegetable oils, polyalkylene glycols, etc. The pharmaceutical preparations can be made in the solid form, for example as tablets, dragees, suppositories, capsules, or in the liquid form, e.g., as solutions, suspensions, or emulsions. They contain moreover, if desired, auxiliary agents, such as preservatives, stabilizers, wetting agents, or emulsifiers, salts for varying osmotic pressure, or buffers. All conventional modes of administration, e.g., to mammals including humans are applicable.

The dosage of the compounds of this invention for all uses, e.g., in human patients, ranges from 5 to 100 mg/day, and a typical unit dosage form contains 1–20 mg of active ingredient.

All of the compounds of this invention are also useful for the preparation of other compounds of this invention and also for preparation of the starting materials from which they were prepared and, as well, for preparation of other ergolinyl or 9,10-didehydroergolinyl compounds.

The compounds of this invention are produced according to conventional methods, e.g., by conventionally reducing an ergoline, unsubstituted in the aromatic ring of the ergoline molecule, and of Formula II

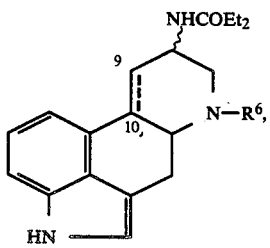

(II)

wherein the 8-positioned urea side chain can be in the α- or β-configuration, $C_9$ === $C_{10}$ as a CC single or C=C double bond, and $R^6$ is as defined above, with sodium borohydride in trifluoroacetic acid to form the 2,3-dihydro compound; and optionally acylating this in the 1-position and/or nitrating it with nitric acid and/or, optionally, saponifying the thus-obtained nitro compound in the 1-position and optionally alkylating it in the 1-positioned nitrogen, and/or optionally, subsequently, reducing the nitro group to the amino group;

or, optionally, a thus-obtained nitro compound is saponified in the 1-position and dehydrogenated in the 2,3-position and the resultant 2,3-dehydrogenated nitro compound is acylated, sulfonylated, or alkylated on the 1-positioned nitrogen, and thereafter the nitro group is reduced to an amino group or the above-obtained 2,3-dehydrogenated nitro compound is halogenated in the 2-position and subsequently the nitro group is reduced to the amino group and optionally a thus-produced amino compound is alkylated or acylated and, if desired, the thus-obtained acyl compound is reduced to the monoalkyl compound; and optionally any such compound is subsequently converted into an acid addition salt. All such reactions are conventional.

The starting materials of Formula II are conventional. They are ergoline-diethylurea derivatives wherein the ureido side chain is either in the α- or β-position, which are saturated or unsaturated in the 9,10-position, and which are substituted on the nitrogen atom in the 6-position by $C_{1-4}$-alkyl. (See, for example DOS No. 1,695,771, German Pat. No. 2,238,540, and DOS No. 2,924,102.)

The indole system of these urea derivatives of Formula II is reduced with sodium borohydride in trifluoroacetic acid in the 2,3-position selectively to the indoline system (DOS No. 2,810,774) and, optionally can be, acylated in the 1-position with a reactive acid derivative, such as acetic anhydride or acetyl chlorine in pyridine.

Nitration of the compounds of Formula II takes place with nitric acid in the presence of sulfuric acid or acetic acid, the reaction yielding, with the use of excess nitric acid, besides the desired nitration in the 12-, 13-, and/or 14-positions, in some cases small amounts of 1-nitro and/or 9-nitro compounds. Mononitration is essentially conducted according to the rules of electrophilic substitution of aniline, wherein primarily the 2,3-dihydroergolines are nitrated in the 13-position, the acylated 2,3-dihydroergolines and the 9,10-didehydro-2,3-dihydroergolines are nitrated in the 12- and 14-position side-by-side. Moreover, small quantities of the remaining position isomers, and dually nitrated products can be formed. Separation is conventionally effected by chromatography or recrystallization.

If the thus-obtained nitro compound contains an acyl group in the 1-position, this group can be saponified with dilute mineral acid, such as 1N hydrochloric acid, or with hydrazine.

The nitro compound unsubstituted in the 1-position can be subsequently reconverted by oxidation into the ergoline or indole system. For this purpose, this compound is reacted in an inert solvent, such as chlorinated hdyrocarbons, with an oxidizing agent, such as pyrolusite, nickel peroxide, derivatives of chromic acid, phenylselenous acid anhydride, palladium salts, oxygen, and catalysts, or with dimethyl sulfide, tert-butyl hypochlorite, and a base.

If desired, the aforementioned compound can again be acylated or alkylated in the 1-position on the indole nitrogen. Alkylation takes place according to Y. Kikugawa et al., Synthesis 1981: 461; acylation takes place according to V.O. Illi, Synthesis 1975: 387.

Subsequently, the nitro group can be reduced selectively, i.e., without reduction of any 9,10-double bond present, to the amino group with sodium borohydride in the presence of metallic salts, such as nickel(II) salts or tin(II) salts (A. Nose et al., Chem. Pharm. Bull. 29: 1155 [1981] and T. Satoh et al., Chem. Pharm. Bull. 29: 1443 [1981]).

However, it is furthermore also possible to halogenate the nitrated ergolinylurea compound in the 2-position. For this purpose, the starting material is dissolved in an inert solvent and reacted with a halogenating agent.

Suitable chlorinating agents include N,2,6-trichloro-4-nitroacetanilide, N'-chlorosuccinimide, N-chlorosaccharin, tert-butyl hypochlorite, N-chloroacetanilide, N-chlorophthalimide, N-chlorotetrachlorophthalimide, 1-chlorobenzotriazole, N-chloro-2,4,6-trichloroacetanilide, thionyl chloride, sulfuryl chloride, sulfuryl chlorofluoride, cyanurtrichloride, copper(II) chloride, hexachloroacetone, tetraalkylammonium perchlorate, such as tetramethylammonium perchlorate, and sodium hypochlorite.

Suitable for introduction of bromine are N-bromosuccinimide, as well as bromine, N-bromoacetamide, N-bromophthalimide, N,N-dibromohydantoin, N-bromo-p-toluene-sulfonamide, N-bromodi-p-toluenesulfimide, pyrrolidone-(2)-hydrotribromide, N-bromocaprolactam, dioxane dibromide, pyridinium bromide, pyridinium perbromide, phenyltrimethylammonium bromide, phenyltrimethylammonium perbromide, 3-bromo-6-chloro-2-methylimidazo[1,2-b]pyridazine as the bromine complex, copper(II) bromide, sodium hypobromide, 5,5-dibromo-2,2-dimethyl-4,6-dioxo-1,3-dioxane, 2,4,4,6-tetrabromocyclohexa-2,5-dienone, 2-carboxyethyltriphenylphosphonium perbromide, tetraalkylammonium perbromide, such as tetramethylammonium perbromide, and 1,3-dibromo-5,5-dimethylhydrantoin.

The halogenating agents can be utilized in various solvents. Suitable solvents are in all cases those that are inert with respect to the reactants. Examples include aliphatic and cyclic ethers, such as diethyl ether, methylethyl ether, tetrahydrofuran, and dioxane, halogenated hydrocarbons, such as methylene chloride, chloroform, and carbon tetrachloride, polar aprotic solvents, such as hexamethylphosphoric triamide, acetonitrile, dimethylformamide, N-methylpyrrolidone, dimethylacetamide, and tetramethylurea, saturated and unsaturated carbocyclic compounds, such as hexane, benzene, and toluene, as well as ketones, such as acetone, cyclohexanone, methyl ethyl ketone, and methyl isobutyl ketone.

The solvents can be used individually or in a mixture with one another.

If desired, the nitro compound, reduced to the amino compound, can be reacted by alkylation and acylation to the corresponding alkyl or acyl compounds. A thus-obtained acylamino compound can optionally be converted into the corresponding monoalkylamino compounds by reduction with diisobutylaluminium hydride, with lithium aluminum hydride, or with borane dimethyl sulfide. Compounds wherein R is a ring system can be formed analogously to preparative methods used for the alkylation. Therefore, the corresponding aminoergolinyl-diethylurea is reacted with an $\alpha,\omega$-dihalogenated straight-chained hydrocarbon in an aprotic solvent under heating in the presence of a proton acceptor (base) like triethylamine, ethyldiisopropylamine and diazobicycloundecene.

Several versions of the conventional process of this invention can be summarized by the following formula scheme:

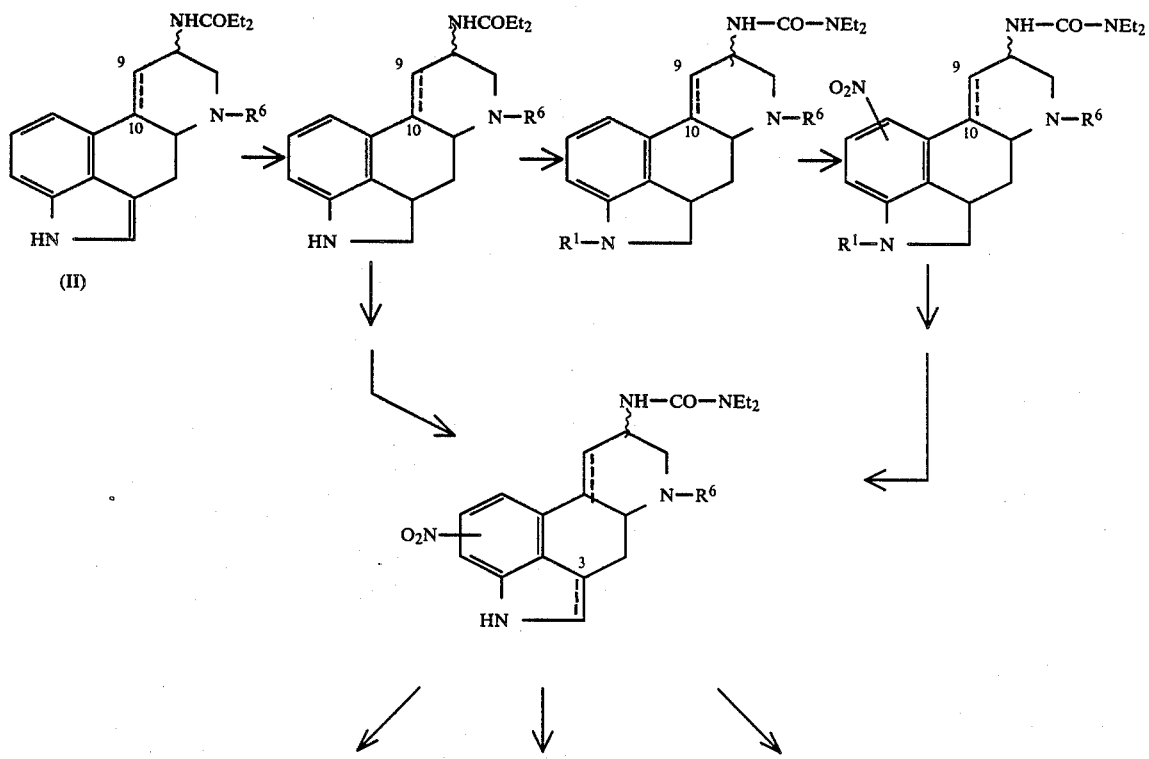

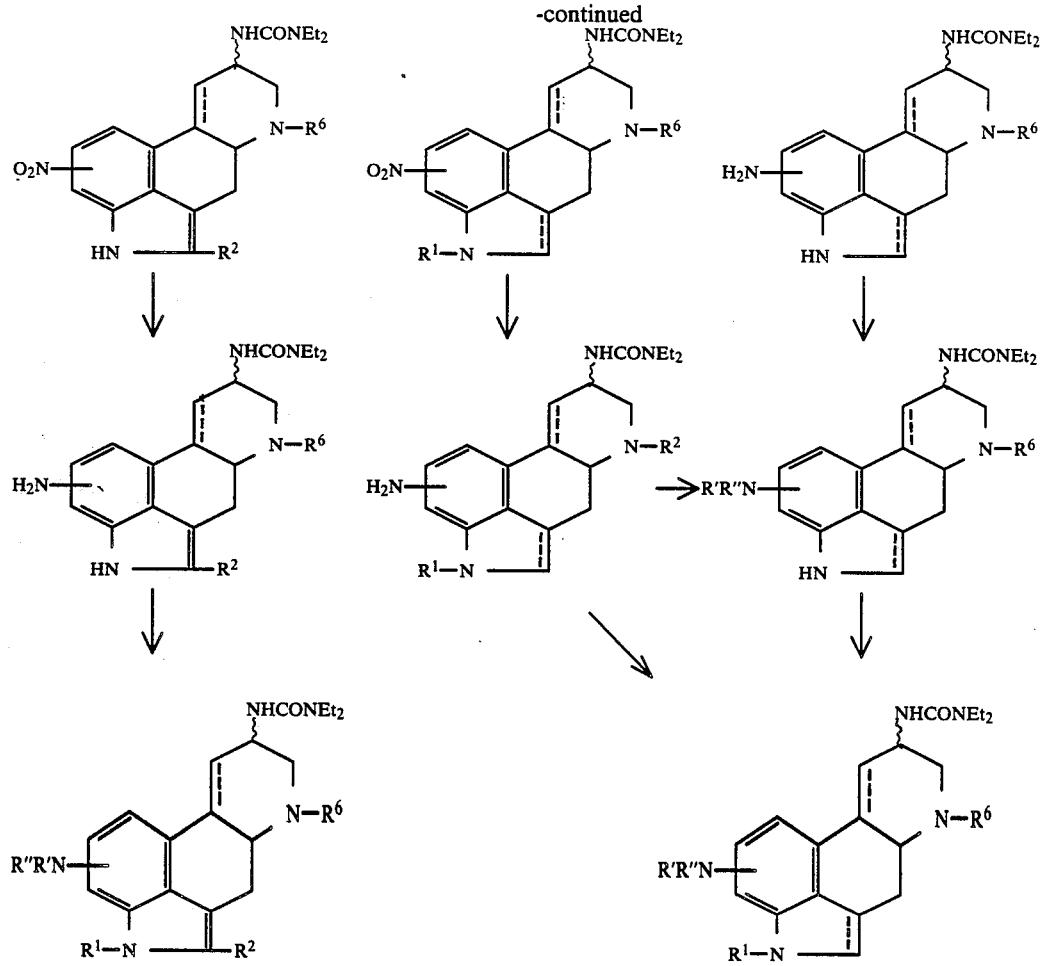

The resultant compounds can be purified either as the free bases or in the form of their acid addition salts, obtained optionally by reaction with a physiologically compatible acid, e.g., tartaric acid, maleic acid, or benzoic acid, etc., by recrystallization and/or chromatography.

In order to form salts, the thus-obtained compound can be dissolved in a small amount of methanol and combined at room temperature with a concentrated solution of the desired organic acid in methanol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

At −20° C., 19.6 g of 3-(9,10-didehydro-6-methyl-8α-ergolinyl)-1,1-diethylurea is dissolved in 80 ml of trifluoroacetic acid, and 8 portions of respectively 500 mg of sodium borohydride are added at intervals of 3-4 minutes. The mixture is then poured on ice, made alkaline under ice cooling with 90 ml of 26% ammonia solution, and extracted with methylene chloride. The organic phase is dried, concentrated, and chromatographed on silica gel with methylene chloride/methanol, thus isolating 10.6 g of 3-(9,10-didehydro-2,3-dihydro-6-methyl-8α-ergolinyl)-1,1-diethylurea as a mixture of isomers of the 3α and 3β-H-compounds. Crystallization from ethyl acetate yields 6.5 g of the 3β-H-compound.

$[\alpha]_D = +207°$ (0.5% in chloroform).

The mother liquor is essentially a mixture of the 3α- and 3β-H-isomeric compounds and can in most cases be used for further reaction stages in the form of a mixture.

In the same way, the following hydrogenated 2,3-dihydro compounds are prepared from the corresponding 2,3-unsaturated ergolines:

3-(2,3-dihydro-6-methyl-8α-ergolinyl)-1,1-diethylurea, $[\alpha]_D = +44°$ (0.5% in chloroform), yield 69%, 30% thereof as the crystalline 3β-H-compound;

3-(2,3-dihydro-6-methyl-8α-ergolinyl)-1,1-diethylurea tartaric acid salt (1:1), $[\alpha]_D = +31°$ (0.5% in pyridine);

3-(9,10-didehydro-2,3β-dihydro-6-methyl-8β-ergolinyl)-1,1-diethylurea, $[\alpha]_D = +10°$ (0.5% in CHCl$_3$);

3-(2,3-dihydro-6-methyl-8β-ergolinyl)-1,1-diethylurea, isolated as a mixture of isomers (3α- and 3β-H);

3-(2,3-dihydro-6-n-propyl-8α-ergolinyl)-1,1-diethylurea, $[\alpha]_D = +14°$ (0.5% in CHCl$_3$).

EXAMPLE 2

One millimole of 3-(9,10-didehydro-2,3β-dihydro-6-methyl-8α-ergolinyl)-1,1-diethylurea is dissolved in 2 ml of pyridine and 2 ml of acetic anhydride, allowed to stand at room temperature for 2 hours, and poured on ice. After 15 minutes of agitation, the mixture is made alkaline with dilute ammonia solution and extracted with methylene chloride, dried, and evaporated.

In a yield of 96%, 3-(1-acetyl-9,10-didehydro-2,3-dihydro-6-methyl-8α-ergolinyl)-1,1-diethylurea is obtained as a crystalline 3β-H-compound. $[α]_D = +190°$ (0.5% in chloroform).

In the same way, the following 1-acetyl-2,3-dihydroergoline derivatives are prepared from the 2,3-dihydroergoline derivatives:

3-(1-acetyl-2,3α-dihydro-6-methyl-8α-ergolinyl)-1,1-diethylurea, yield 85%, $[α]_D = +46°$ (0.5% in chloroform);

3-(1-acetyl-2,3β-dihydro-6-methyl-8α-ergolinyl)-1,1-diethylurea, $[α]_D = -61°$ (0.5% in chloroform).

EXAMPLE 3

Under ice cooling, 10 mmol of 3-(2,3-dihydro-6-methyl-8α-ergolinyl)-1,1-diethylurea is dissolved in 100 ml of concentrated sulfuric acid; 7 ml of a solution of 10 ml of 65% nitric acid in 90 ml of concentrated sulfuric acid is added thereto, and the mixture is stirred for 15 minutes in an ice bath. The reaction solution is then slowly introduced dropwise into ice, made alkaline under ice cooling with 32% ammonia solution, and extracted by shaking with methylene chloride. After washing the organic phase with water and drying with magnesium sulfate, the nitrated compound is obtained in a 90% crude yield. After chromatographic separation and purification, respectively, 3-(2,3-dihydro-6-methyl-13-nitro-8α-ergolinyl)-1,1-diethylurea is obtained in a 71% yield.

$[α]_D = +52°$ (0.5% in chloroform).

EXAMPLE 4

Analogously, nitration of the corresponding ergoline derivatives unsubstituted in the 12-, 13-, and 14-positions yields the following compounds:

I. 3-(1-Acetyl-2,3-dihydro-6-methyl-12-nitro-8α-ergolinyl)-1,1-diethylurea as an isomer mixture of the 3α- and 3β-H-compounds.

II. 3-(9,10-Didehydro-2,3β-dihydro-6-methyl-12-nitro-8α-ergolinyl)-1,1-diethylurea; $[α]_D = -674°$ (0.5% in CHCl$_3$). Yield: 50%.

III. 3-(9,10-Didehydro-2,3-dihydro-6-methyl-14-nitro-8α-ergolinyl)-1,1-diethylurea. Yield: 17%.

IV. 3-(2,3β-Dihydro-6-methyl-13-nitro-8β-ergolinyl)-1,1-diethylurea. Yield: 53%. $[α]_D = +70°$ (0.5% in 1N HCl).

3-(2,3α-Dihydro-6-methyl-13-nitro-8β-ergolinyl)-1,1-diethylurea. Yield: 15%. $[α]_D = -150°$ (0.5% in CHCl$_3$).

V. 3-(9,10-Didehydro-2,3β-dihydro-6-methyl-12-nitro-8β-ergolinyl)-1,1-diethylurea. Yield: 30%. $[α]_D = -593°$ (0.5% in MeOH) as the tartaric acid salt.

VI. 3-(2,3α-Dihydro-13-nitro-6-n-propyl-8α-ergolinyl)-1,1-diethylurea. Yield: 50%. $[α]_D = -156°$ (0.5% in CHCl$_3$).

3-(2,3β-Dihydro-13-nitro-6-n-propyl-8α-ergolinyl)-1,1-diethylurea. Yield: 38%. $[α]_D = +86°$ (0.5% in CHCl$_3$).

EXAMPLE 5

One millimole of 3-(1-acetyl-2,3β-dihydro-6-methyl-12-nitro-8α-ergolinyl)-1,1-diethylurea is heated in a mixture of 2 ml of anhydrous hydrazine and 2 ml of chloroform for 3 hours to 50° C., poured into water, extracted with methylene chloride, the organic phase is dried, and evaporated under vacuum, yielding 230 mg of 3-(2,3-dihydro-6-methyl-12-nitro-8α-ergolinyl)-1,1-diethylurea. Yield: 25%. $[α]_D = +538°$ (0.5% in methanol) as the tartaric acid salt.

EXAMPLE 6

One millimole of 3-(1-acetyl-2,3-dihydro-6-methyl-12-nitro-8α-ergolinyl)-1,1-diethylurea, dissolved in 5 ml of 1N hydrochloric acid, is heated for one hour to 95° C. After cooling, the mixture is made alkaline with dilute ammonia solution, combined with methylene chloride, and extracted. After drying the organic phase, the latter is evaporated, thus obtaining 220 mg of 3-(2,3-dihydro-6-methyl-12-nitro-8α-ergolinyl)-1,1-diethylurea.

EXAMPLE 7

One millimole of 3-(2,3-dihydro-6-methyl-13-nitro-8α-ergolinyl)-1,1-diethylurea is dissolved in 10 ml of methylene chloride, and 2 g of pyrolusite in solid form is added thereto. The mixture is then stirred for 2 hours at room temperature. After removing excess pyrolusite by filtration, the filtrate is evaporated. The residue is chromatographed on silica gel with methylene chloride/methanol (5%), thus obtaining 210 mg of 3-(6-methyl-13-nitro-8α-ergolinyl)-1,1-diethylurea.

$[α]_D = -2°$ (0.5% in chloroform).

Analogously, the following compounds are produced from the corresponding 2,3-dihydroergolines:

1,1-diethyl-3-(6-methyl-12-nitro-8α-ergolinyl)urea, yield: 50%;

3-(9,10-didehydro-6-methyl-12-nitro-8α-ergolinyl)-1,1-diethylurea, yield: 49%, $[α]_D = -344°$ (0.2% in CHCl$_3$);

3-(9,10-didehydro-6-methyl-14-nitro-8α-ergolinyl)-1,1-diethylurea, yield: 30%, $[α]_D = +336°$ (0.5% in chloroform);

1,1-diethyl-3-(6-methyl-12,14-dinitro-8α-ergolinyl)urea, yield: 27%;

1,1-diethyl-3-(6-methyl-13-nitro-8α-ergolinyl)urea, yield: 46%, $[α]_D = +4.5°$ (0.5% in CHCl$_3$);

3-(9,10-didehydro-6-methyl-12-nitro-8β-ergolinyl)-1,1-diethylurea, yield: 73%, $[α]_D = -646°$ (0.5% in CHCl$_3$);

1,1-diethyl-3-(13-nitro-6-n-propyl-8α-ergolinyl)urea, yield: 70%, $[α]_D = +2°$ (0.5% in CHCl$_3$).

EXAMPLE 8

A solution is prepared from 150 mg of 3-(9,10-didehydro-2,3-dihydro-6-methyl-14-nitro-8α-ergolinyl)-1,1-diethylurea in 5 ml of methylene chloride; 250 mg of pyridinium dichromate, dissolved in 2 ml of methylene chloride, is added to the reaction mixture and the latter is agitated for one hour at room temperature. Then the mixture is diluted with water, extracted by shaking with methylene chloride, the organic phase is dried and evaporated. The residue is chromatographed on silica gel with methylene chloride/methanol (5%), thus obtaining 70 mg of 3-(9,10-didehydro-6-methyl-14-nitro-8α-ergolinyl)-1,1-diethylurea.

EXAMPLE 9

A solution of 0.4 mmol of tert-butyl hypochlorite in 2 ml of methylene chloride is added dropwise to a solution of 0.3 mmol of 3-(2,3-dihydro-6-methyl-13-nitro-8β-ergolinyl)-1,1-diethylurea, 0.4 mmol of dimethyl sulfide, and 0.3 mmol of triethylamine in 5 ml of methylene choride at −70° C., and the mixture is agitated for 2 hours. Then a solution of 2 mmol of sodium ethylate in 2 ml of ethanol is added thereto within 10 minutes, and the mixture is warmed up to room temperature within 2 hours, whereafter it is combined with water, extracted with methylene chloride, the organic phase is dried and evaporated. Chromatography on silica gel with methylene chloride/methanol (5%) yields 30 mg of 3-(6-methyl-13-nitro-8β-ergolinyl)-1,1-diethylurea.

EXAMPLE 10

One millimole of 3-(2,3β-dihydro-6-methyl-12-nitro-8α-ergolinyl)-1,1-diethylurea is dissolved in 25 ml of methanol, cooled in an ice bath, and 2 mmol of nickel chloride (with 6H$_2$O) and thereafter 5 mmol of sodium borohydride are added thereto in 4–5 portions. Under ice cooling, the mixture is acidified with 2N hydrochloric acid, combined with dilute ammonia solution, and extracted by shaking. After drying and evaporation of the organic phase, 350 mg of 3-(12-amino-2,3-dihydro-6-methyl-8α-ergolinyl)-1,1-diethylurea is obtained. $[\alpha]_D = -31°$ (0.5% methanol) as the tartaric acid salt (1:1).

Analogously, the following aminoergolines are produced from the corresponding nitro compounds:

3-(13-amino-2,3-dihydro-6-methyl-8α-ergolinyl)-1,1-diethylurea, yield: 64%;

3-(12-amino-9,10-didehydro-2,3-dihydro-6-methyl-8α-ergolinyl)-1,1-diethylurea, yield: 48%;

3-(1-acetyl-13-amino-2,3-dihydro-6-methyl-8α-ergolinyl)-1,1-diethylurea, yield: 81%, $[\alpha]_D = +14°$ (0.5% in chloroform);

3-(1-acetyl-12-amino-9,10-didehydro-2,3-dihydro-6-methyl-8α-ergolinyl)-1,1-diethylurea, yield: 65%, $[\alpha]_D = +111°$ (0.5% in chloroform);

3-(12-amino-6-methyl-8α-ergolinyl)-1,1-diethylurea, yield: 83%;

3-(13-amino-6-methyl-8α-ergolinyl)-1,1-diethylurea, yield: 68%, $[\alpha]_D = 0°$ (0.5% in chloroform).

3-(12-amino-9,10-didehydro-6-methyl-8α-ergolinyl)-1,1-diethylurea, yield: 53%; from this, the tartaric acid salt (1:1), yield: 83%, $[\alpha]_D = -320°$ (0.5% in pyridine);

3-(14-amino-9,10-didehydro-6-methyl-8α-ergolinyl)-1,1-diethylurea, yield: 65%, $[\alpha]_D = -305°$ (0.5% in CHCl$_3$);

3-(12,14-diamino-6-methyl-8α-ergolinyl)-1,1-diethylurea, yield: 56%;

3-(13-amino-6-methyl-8β-ergolinyl)-1,1-diethylurea, yield: 82%, $[\alpha]_D = 0°$ (0.5% in pyridine) as the tartaric acid salt;

3-(13-amino-1,6-dimethyl-8α-ergolinyl)-1,1-diethylurea, yield: 64%, $[\alpha]_D = -8°$ (0.5% in CHCl$_3$);

3-(12-amino-9,10-didehydro-6-methyl-8α-ergolinyl)-1,1-diethylurea, yield: 36%, $[\alpha]_D = -605°$ (0.5% in MeOH);

3-(1-acetyl-13-amino-6-methyl-8α-ergolinyl)-1,1-diethylurea, yield: 48%, $[\alpha]_D = -28°$ (0.5% in CHCl$_3$);

3-(13-amino-6-n-propyl-8α-ergolinyl)-1,1-diethylurea, yield: 80%, $[\alpha]_D = -2°$ (0.5% in CHCl$_3$);

3-(12-amino-2-bromo-9,10-didehydro-6-methyl-8α-ergolinyl)-1,1-diethylurea, yield: 63%, $[\alpha]_D = -305°$ (0.5% in CHCl$_3$).

EXAMPLE 11

355 mg of 3-(13-amino-6-methyl-8α-ergolinyl)-1,1-diethylurea is dissolved in 10 ml of tetrahydrofuran, 0.5 ml of ethyldiisopropylamine ("Hünig" base) and 1 ml of methyl iodide are added thereto, and the mixture is heated to boiling for 3 hours. The primary amount of solvent is removed by evaporation, the mixture is distributed between methylene chloride and dilute ammonia solution, the organic phase is separated, and dried. After evaporation, the product is chromatographed on silica gel with methylene chloride and methanol (5%), thus obtaining 310 mg of 1,1-diethyl-3-(13-dimethylamino-6-methyl-8α-ergolinyl)urea, yield: 73%.

EXAMPLE 12

353 mg of 3-(12-amino-9,10-didehydro-6-methyl-8α-ergolinyl)-1,1-diethylurea is dissolved in 5 ml of anhydrous pyridine, 5 ml of acetic anhydride is added, and the mixture is allowed to stand at room temperature for 2 hours. Then the mixture is stirred into ice, again allowed to stand for 15 minutes, and distributed between methylene chloride and bicarbonate solution. The organic phase is dried, evaporated, and chromatographed as in Example 9, thus obtaining 250 mg of 3-(12-acetylamino-9,10-dihdehydro-6-methyl-8α-ergolinyl)-1,1-diethylurea by recrystallization from ethyl acetate/diisopropyl ether.

$[\alpha]_D = +226°$ (0.5% in methanol).

EXAMPLE 13

200 mg of 3-(12-acetylamino-9,10-didehydro-6-methyl-8α-ergolinyl)-1,1-diethylurea is dissolved in 10 ml of dioxane, combined with 2 ml of 20% diisobutyl aluminum hydride solution in toluene, and heated to 100° C. for 7 hours. The mixture is allowed to cool, then, under cooling, first water, thereafter 2N hydrochloric acid are added thereto, and the solution is rendered alkaline with dilute ammonia, after adding about 1 g of tartaric acid. The mixture is extracted by shaking with methylene chloride, the organic phase is dried and evaporated. The residue is charomatographed as disclosed in Example 7, thus producing 135 mg of 3-(9,10-didehydro-12-ethylamino-6-methyl-8α-ergolinyl)-1,1-diethylurea.

$[\alpha]_D = +135°$ (0.5% in CHCl$_3$).

EXAMPLE 14

At −20° C., 355 mg of 3-(13-amino-6-methyl-8α-ergolinyl)-1,1-diethylurea is reacted to the N-formyl compound with the mixed anhydride of acetic acid and formic acid and the N-formyl compound is reduced with borane-dimethyl sulfide (S. Krishnamurty, Tetrahedron Letters 1982: 3315). After chromatography, 260 mg of 1,1-diethyl-3-(6-methyl-13-methylamino-8α-ergolinyl)urea is obtained.

N-Formyl compound: yield: 66%, $[\alpha]_D = -25°$ (0.5% in methanol).

N-Methyl compound: yield: 74%, $[\alpha]_D = -15°$ (0.5% in CHCl$_3$).

EXAMPLE 15

A solution is prepared from 410 mg of 3-(13-nitro-6-methyl-8α-ergolinyl)-1,1-diethylurea in 10 ml of methylene chloride, 40 mg of tetrabutylammonium hydrogen sulfate and 0.8 ml of acetyl chloride are added, and this mixture is poured on 1 g of pulverized potassium hydroxide. After 1.5 hours of agitation at room temperature, the mixture is diluted with sodium bicarbonate solution, the organic phase is separated and dried with sodium sulfate. After evaporation and chromatography as indicated in Example 9, 375 mg of 3-(1-acetyl-6-methyl-13-nitro-8α-ergolinyl)-1,1-diethylurea is obtained.

$[\alpha]_D = -34°$ (0.5% in CHCl$_3$).

EXAMPLE 16

Analogously to Example 15, alkylation is conducted with methyl iodide in tetrahydrofuran, thus obtaining 335 mg of 1,1-diethyl-3-(1,6-dimethyl-13-nitro-8α-ergolinyl)urea. $[\alpha]_D = -15°$ (0.5% in CHCl$_3$).

EXAMPLE 17

500 mg of 3-(9,10-didehydro-6-methyl-12-nitro-8α-ergolinyl)-1,1-diethylurea is dissolved in 10 ml of dioxane and at room temperature 650 mg of pyrrolidone hydroperbromide in solid form is added to the reaction solution. The latter is stirred for 4 hours, 1 ml of acetone is added, and the main quantity of the solvent is evaporated. The residue is distributed between methylene chloride and bicarbonate solution, the organic phase is dried and evaporated. The residue is chromatographed on silica gel with methylene chloride and methanol, thus obtaining 110 mg of 3-(2-bromo-9,10-didehydro-6-methyl-12-nitro-8α-ergolinyl)-1,1-diethylurea.

$[\alpha]_D = -300°$ (0.2% in methanol).

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A substituted ergoline of the formula

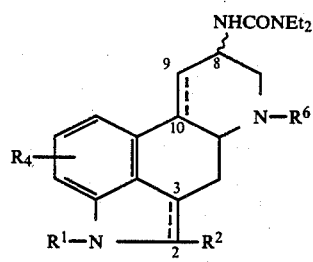

wherein
the urea side chain in the 8-position is in the α- or β-configuration,
$C_2 \text{---} C_3$ and $C_9 \text{---} C_{10}$ each independently is a CC single or C=C double bond,
R is NO$_2$ or NR'R",
R' and R" each independently is hydrogen, C$_{1-4}$-alkyl, C$_{3-4}$-cycloalkyl C$_{1-5}$-alkanoyl, C$_{7-10}$-aroyl or C$_{7-10}$-aralkanoyl, or, R' and R" together with the connecting N-atom form a 3- to 9-membered C-atom ring, optionally substituted by an alkyl group, the total number of carbon atoms being up to 10 in all cases,
R$^1$ is hydrogen, C$_{1-4}$-alkyl C$_{3-4}$-cycloalkyl, C$_{1-5}$-alkanoyl, C$_{7-10}$-aroyl, C$_{7-10}$-aralkanoyl, C$_{6-8}$-aryl- or C$_{1-4}$-alkylsulfonyl,
R$^2$ is hydrogen or halogen when $C_2 \text{===} C_3$ is a C=C double bond, or hydrogen when $C_2 \text{===} C_3$ is a CC single bond, and
R$^6$ is C$_{1-4}$-alkyl C$_{3-4}$-cycloalkyl,
n is 1 or 2 or a physiologically acceptable acid addition salt thereof.

2. A compound of claim 1, wherein alkyl is methyl, ethyl, n-propyl, isopropyl, n-butyl, isobutyl, tertbutyl or cyclopropylmethyl.

3. A compound of claim 1, wherein R is aziridine, pyrrolidine or piperidine.

4. A compound of claim 1, wherein the alkanoyl group is acetyl, propanoyl, n-butanoyl or isobutanoyl.

5. A compound of claim 1, wherein ar(alkan)oyl is benzoyl, p-methylbenzoyl, 3,5-dimethylbenzoyl, phenylacetyl, phenylpropanoyl, or p-tolylacetyl.

6. A compound of claim 1, wherein the sulfonyl group is methanesulfonyl or p-toluenesulfonyl.

7. A compound of claim 1, wherein halo is chlorine or bromine.

8. 3-(9,10-Didehydro-6-methyl-12-nitro-8α-ergolinyl)-1,1-diethylurea, a compound of claim 1.

9. 3-(12-Amino-9,10-didehydro-6-methyl-8α-ergolinyl)-1,1-diethylurea tartrate, a compound of claim 1.

10. 3-(6-Methyl-13-nitro-8α-ergolinyl)-1,1-diethylurea, a compound of claim 1.

11. 3-(13-Amino-6-methyl-8α-ergolinyl)-1,1-diethylurea, a compound of claim 1.

12. A pharmaceutical composition comprising an amount of a 9,10-didehydro compound of claim 1 effective as an antidepressant and a pharmaceutically acceptable carrier.

13. A pharmaceutical composition comprising an amount of an ergolinyl compound of claim 1 effective as a neuroleptic and a pharmaceutically acceptable carrier.

14. A method of treating depression in a patient in need of such treatment comprising administering an effective amount of a 9,10-didehydro compound of claim 1.

15. A method of treating a neuroleptic disturbance in a patient in need of such treatment comprising administering an effective amount of an ergolinyl compound of claim 1.

16. A substituted ergoline of the formula

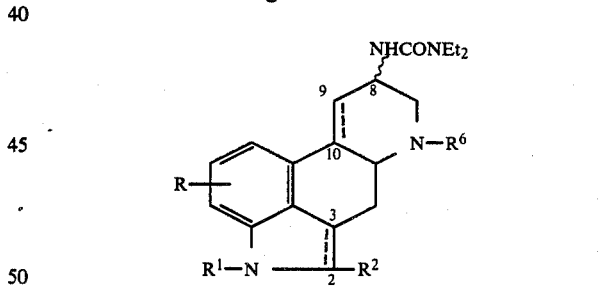

wherein
the urea side chain in the 8-position is in the α- or β-configuration,
$C_9 \text{===} C_{10}$ is a CC single or C=C double bond,
R is hydrogen, NO$_2$ or NR'R",
R' and R" each independently is hydrogen, C$_{1-4}$-alkyl C$_{3-4}$-cycloalkyl, C$_{1-5}$-alkanoyl, C$_{7-10}$-aroyl or C$_{7-10}$-aralkanoyl, or, R' and R" together with the connecting N-atom form a 3- to 9-membered C-atom ring, optionally substituted by an alkyl group, the total number of carbon atoms being up to 10 in all cases,
R$^1$ is hydrogen, C$_{1-4}$-alkyl C$_{3-4}$-cycloalkyl, C$_{1-5}$-alkanoyl, C$_{7-10}$-aroyl, C$_{7-10}$-aralkanoyl, C$_{6-8}$-aryl- or Cl-4-alkylsulfonyl,
R$^2$ is hydrogen, and
R$^6$ is C$_{1-4}$-alkyl C$_{3-4}$-cycloalkyl, or a physiologically acceptable acid addition salt thereof.

17. A compound of claim 1 wherein R is $NO_2$, $NH_2$, $N(CH_3)_2$ or $NH(COCH_3)$.

18. A compound of claim 1 containing two R groups.

19. A compound of claim 1 wherein $C_9\text{===}C_{10}$ is a double bond.

20. A compound of claim 1 wherein $C_9\text{===}C_{10}$ is a single bond.

21. A pharmaceutical composition comprising an amount of a 9,10-didehydro compound of claim 16 effective as an antidepressant and a pharmaceutically acceptable carrier.

22. A pharmaceutical composition comprising an amount of a compound of claim 16 effective as a neuroleptic and a pharmaceutically acceptable carrier.

23. A method of treating depression in a patient in need of such treatment comprising administering an effective amount of a 9,10-didehydro compound of claim 16.

24. A method of treating a neuroleptic disturbance in a patient in need of such treatment comprising administering an effective amount of an ergolinyl compound of claim 16.

* * * * *